Oct. 30, 1951 W. S. HAHN Plant Pat. 1,046
IVY PLANT
Filed July 10, 1950
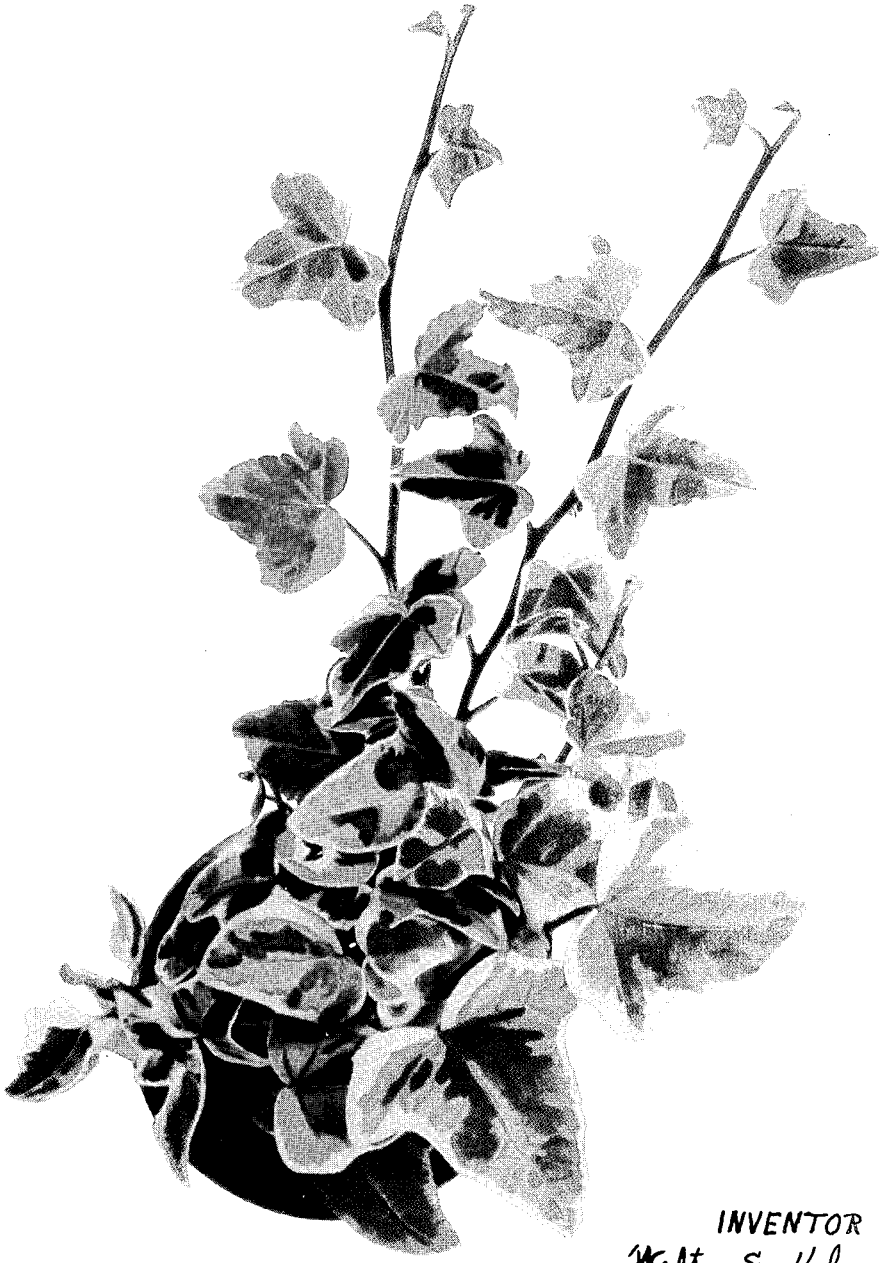
INVENTOR
Walter S. Hahn
By Orville M. Kile
Plant Pat. Agt.

Patented Oct. 30, 1951

Plant Pat. 1,046

UNITED STATES PATENT OFFICE 1,046

IVY PLANT

Walter S. Hahn, Pittsburgh, Pa., assignor to
Louis Hahn & Son, Pittsburgh, Pa.

Application July 10, 1950, Serial No. 172,797

1 Claim. (Cl. 47—59)

This new variety was discovered by me as a sport of Hahn's Self-Branching Ivy (unpatented), in my extensive greenhouses in the suburbs of Pittsburgh, Pennsylvania, where I keep constant watch for such new and promising sports. It has been reproduced by me by means of cuttings, at these greenhouses. It is a strong, vigorous grower and has for a number of years proved hardy in this latitude.

The illustration shows a potted specimen about nine weeks old, grown under average conditions. Only part of the leaves have been tinted in an effort to show the variegated effect. The untinted leaves give a truer portrayal of the powdery, silver-gray bloom on the leaves. While the central stems and petioles have also been tinted, the artist was unable to bring out fully the greenish-brown effect of the stems with reddish tints at the nodes and on the petioles. These colorings are quite noticeable on most specimens.

This new variegated variety is particularly notable for its relatively small leaves arranged rather far apart on the central stems and with little branching fill-in between leaves, except at certain seasons, which results in rapid growth to marketable size; the peculiar, irregular patterns of the variegation of the leaves and the powdery silver-gray bloom on the leaves; together with the touches of reddish color on the younger branches, particularly at the nodes and on the petioles.

The leaves are irregularly three-lobed, seldom showing any tendency toward additional lateral lobes. The central lobe is much longer and more prominent than the other two, lanceolate, and frequently terminating in a point curving sidewise. In fact few leaves are symmetrical. Undulate rather than flat.

The largest leaves measure 2 inches long by 2 inches from tip to tip of the lateral lobes, but most of the leaves on a ten weeks old plant will be nearer 1¼ inches in both dimensions. The petioles are slender and for the fourth leaf from the end of a branch measure ¾ of an inch to 1 inch in length, becoming longer as the plant matures. The largest leaves at the base of a three-month plant would have petioles about 2 inches long.

The veining of the leaves is not notably prominent or much raised above the leaf surface. The substance of the leaves may be described as tender rather than heavy or leathery, but leaves are substantial and stand up well when the variety is used as a house plant.

Nearly every leaf is distinguished by a border of white, varying on a single leaf from a line so narrow at points as to be almost invisible to a width at another point extending half way, or in some instances all the way, to the central vein. This irregularity of the white margin is one of the readily distinguishing features of this variety. There is no regular wide "band" of white extending around the margin of the leaf and following its contour, and the net effect is to show less white than is shown in Plant Patent No. 807, for instance. Also the irregularity of the white pattern gives a pleasingly novel effect.

Within this very irregular, whitish margin there are two distinct and contrasting shades of green, occurring in very irregular spots or blotches, as clearly shown in the illustrations. The lighter of these two shades is approximately Deep Glaucous-Gray, Plate XLVIII, in Ridgway's Color Standards and Nomenclature; the darker is approximately Forest Green, Plate XVII, in Ridgway's. The whitish areas vary from almost pure white to slight tints of yellowish green.

The surfaces of the leaves are not glossy. On the contrary, they give the appearance and effect of having a dull silver-gray, powdery "bloom," although this is not the type of bloom that can be wiped off or destroyed by rubbing as in the case of the bloom on an apple or plum.

The specimen shown in the illustration shows no self-branching except near the base of the plant. This is typical except for certain very favorable seasons of the year when this variety branches freely. But it normally produces far less branching than any other variegated variety known to me, and therefore is able to make much greater growth of the central stems or runners during the first two or three months of its life. This, together with inherent qualities of sturdiness, result in a substantial plant of marketable size at an earlier age than is possible with any other variegated variety known to me.

Having thus disclosed my discovery, I claim:

The new and distinct variety of ivy plant of the variegated type, herein shown and described, characterized particularly by the rapid and vigorous growth of its central stems in its early life; relatively small leaves, widely spaced between internodes and borne on rather short, slender, reddish petioles; and by the notably irregular pattern of variegation of its leaves and the non-glossy, silver-gray bloom effect.

WALTER S. HAHN.

No references cited.